United States Patent [19]

Rubinstein

[11] Patent Number: 5,281,392

[45] Date of Patent: Jan. 25, 1994

[54] METHOD FOR DISINFECTING RED BLOOD CELLS, BLOOD PRODUCTS, AND CORNEAS

[76] Inventor: Alan I. Rubinstein, 10600 Wilshire Blvd., #202, Los Angeles, Calif. 90024

[21] Appl. No.: 858,111

[22] Filed: Mar. 26, 1992

Related U.S. Application Data

[63] Continuation-in-part of Ser. No. 696,856, May 7, 1991, which is a continuation-in-part of Ser. No. 556,756, Jul. 23, 1990, Pat. No. 5,211,912, which is a continuation-in-part of Ser. No. 492,723, Mar. 13, 1990, Pat. No. 5,185,371, which is a continuation-in-part of Ser. No. 230,839, Aug. 9, 1988, Pat. No. 4,971,760, which is a continuation-in-part of Ser. No. 892,058, Aug. 1, 1986, abandoned, which is a continuation-in-part of Ser. No. 838,253, Mar. 10, 1986, abandoned.

[51] Int. Cl.$^5$ .................................................. A61L 2/18
[52] U.S. Cl. ........................................ 422/28; 422/37; 435/2; 435/288; 530/385
[58] Field of Search ............... 422/28, 37; 435/2, 288; 530/385

[56] References Cited

U.S. PATENT DOCUMENTS

| | | |
|---|---|---|
| Re. 27,359 | 5/1972 | Ilg . |
| Re. 31,779 | 12/1984 | Alliger ............ 525/187.23 |
| 3,031,378 | 4/1962 | Ishidate . |
| 3,100,737 | 11/1961 | Auerswald et al. . |
| 4,314,997 | 2/1982 | Shanbrom . |
| 4,481,189 | 11/1984 | Prince . |
| 4,632,980 | 12/1986 | Zee et al. ............ 530/380 |
| 4,675,159 | 6/1987 | Al-Sioufi ............ 422/36 |
| 4,833,165 | 5/1989 | Louderback ......... 514/694 |
| 4,944,920 | 7/1990 | Rubinstein ............ 422/37 |
| 4,971,760 | 11/1990 | Rubinstein ............ 422/37 |
| 5,019,402 | 5/1991 | Kross et al. ......... 424/665 |

FOREIGN PATENT DOCUMENTS

WO85/04107 9/1985 PCT Int'l Appl. .

OTHER PUBLICATIONS

Inactivation of Lymphadenopathy Associated Virus by Chemical Disinfectants: Spire et al.: no date: The Lancet: 899–901.
Disinfection and Inactivation of the Human T Lymphotropic Virus Type III/Lymphadenopathy–Associated Virus: Martin et al.; no date; The Journal of Infectious Diseases; 400–403.

*Primary Examiner*—Jill A. Johnston

[57] ABSTRACT

A process to inactivate viruses or bacteria by disinfecting whole blood products and blood products, including red blood cells, plasma and plasma fractions is disclosed. The process includes providing a disinfectant composition may also be applied to plasma fractions.

8 Claims, No Drawings

METHOD FOR DISINFECTING RED BLOOD CELLS, BLOOD PRODUCTS, AND CORNEAS

RELATED APPLICATIONS

This is a continuation-in-part of U.S. patent application Ser. No. 07/696,856 filed May 7, 1991 which in turn is a continuation-in-part of U.S. patent application Ser. No. 07/556,756 filed Jul. 23, 1990 now U.S. Pat. No. 5,211,912, which in turn is a continuation-in-part of U.S. patent application Ser. No. 07/492,723 filed Mar. 13, 1990, now U.S. Pat. No. 5,185,371, which in turn is a continuation-in-part of U.S. patent application Ser. No. 07/230,839 filed Aug. 9, 1988, now U.S. Pat. No. 4,971,760, which in turn is a continuation-in-part of U.S. patent application Ser. No. 06/892,058 filed Aug. 1, 1986, now abandoned, which in turn is a continuation-in-part of U.S. patent application Ser. No. 06/838,253 filed Mar. 10, 1986, now abandoned.

BACKGROUND

1. Field of the Invention

The present invention relates generally to processing and disinfecting human blood products. More particularly, this invention relates to disinfecting whole blood, blood cells, plasma proteins, and plasma so that they may be used safely and effectively for diagnostic, therapeutic or research purposes. 2. Description of the Related Art Blood products from human and animal donors are widely used for therapeutic, diagnostic and experimental purposes. A persistent problem associated with using blood products from human and animal donors is that these products are subject to contamination by blood-borne viruses and other micro-organisms such as bacteria.

Of particular threat are viruses that appear to cause various forms of hepatitis, including the hepatitis B virus; the non-A, non-B hepatitis virus or viruses. Others of interest are cytomegalovirus and Epstein-Barr virus.

Viruses linked with the incurable and often fatal disease known as acquired immune deficiency syndrome or "AIDS" are probably caused by a retrovirus or group of retroviruses previously denominated "HTLV-III" and other HTLV types—and more currently "HIV" "HIV-1" and "HIV-2." The most common cause of AIDS is thought to be HTLV-III, now usually called HIV-1.

Detection and isolation of such cytopathic retroviruses from patients with AIDS, and certain members of groups that are at high risk for AIDS, have been frequently reported. One such report appears in *Science* 224:500-03 (1984). Such findings are corroborated by P. S. Savin, et al., in an article entitled "Human T-Lymphotrophic Retroviruses in Adult T-cell Leukemia-Lymphoma and Acquired Immune Deficiency Syndrome," *J. Clinical Immunol.* 4:415-23 (1984). Yet another report is by F. Wong-Staal and R. C. Gallo, "Human T-Lymphotrophic Retroviruses," *Nature* 317:395-402 (1985).

The threat of hepatitis, AIDS, and bacterial transmission through transfusion and administration of blood products is not limited to blood cells but extends to the administration of plasma and plasma fractions such as Factor VIII concentrates, Factor IX concentrates, gamma globulin, and antithrombin III.

Disinfecting whole blood and blood products, including red blood cells, plasma, and plasma fractions with disinfectants strong enough to significantly inactivate viruses, bacteria and other organisms has generally been discounted because they have been believed to damage cellular blood constituents or inactivate plasma and plasma protein factions. Additionally, the presence of any residual disinfectant in the blood product to be transfused could be hazardous to the recipient of the transfusion.

One disinfectant in use for blood products is beta-propiolactone. Beta-propiolactone, however, is a known carcinogen and hence potentially very dangerous. To the extent that significant residual amounts of this material may remain in the blood product which is actually transfused, the use of propiolactone represents a potential hazard.

U.S. Pat. No. 4,833,165 relates to using as little as 0.1% formaldehyde and/or phenol to inactivate HTLV-III in blood. However, recently available data and information indicate that red blood cells treated with as little as 0.02% formaldehyde and 0.01% phenol are not viable and not suitable for transfusion.

Applicant's former applications disclose the utility of normal saline and other isotonic solutions of chlorine dioxide for sterilizing certain blood products and tissue products. Quite unexpectedly, chlorine dioxide, a disinfectant strong enough to inactivate blood born viruses and microorganisms, can be utilized to disinfect cellular blood products without destroying the vitality and integrity of the cells.

There is a continuing need to provide systems for disinfecting blood products. In particular, there is a need to disinfect human and animal plasmas fractions so that they can be safely and effectively utilized by a recipient or handled by a user without exposure to harmful viruses and micro-organisms.

SUMMARY OF THE DISCLOSURE

It is the object of this invention to provide compositions and methods to disinfect blood products for their safe and effective use. The invention is based upon the surprising and unexpected discovery that oxidizing compounds, which heretofore have been discounted as blood product disinfectants may be used for disinfecting blood and blood products, including red blood cells, platelets and plasma, without a resulting loss in red blood cell viability or plasma activity. Additionally, oxidizing compounds can be used to disinfectant plasma proteins such as Factor VIII, gamma globulins more specifically IV IgG, Factor IX, and antithrombin III without denaturing the protein or otherwise diminishing the protein physiological activity.

The present invention is based upon the discovery that whole blood and blood products can be disinfected by providing a disinfectant compositions of an oxidizing compound and a diluent, and then mixing whole blood or blood product with the disinfecting compositions for a length of time sufficient to inactivate any bacteria and virus present in the blood or blood product. After the blood or blood product is disinfected, the oxidizing compound is separated form the disinfecting composition, thereby providing blood or blood product which is safe and effective for therapeutic or diagnostic use.

For disinfecting red blood cells, diluents are aqueous solutions of an isotonic effective concentration of solute. More particularly, these diluents include solute which, when dissolved in water at an isotonic effective concentration form solutions which are isotonic with blood. Surprisingly processes utilizing isotonic solutions of an oxidizing compound will not only disinfect red blood cells but will do so without damage to red blood cells. With respect to plasma and plasma proteins fractions, the disinfectant composition need not be isotonic with respect to blood and water or sterile water is a suitable diluent for such compositions. Accordingly, disinfectant compositions consisting of an oxidizing compound in sterile distilled water will effectively disinfect plasma and plasma protein fractions without a resulting loss in physiological activity of the plasma.

This invention may be practiced using economical procedures which are easily adapted to existing techniques for handling blood and blood products including red blood cells and plasma. Moreover, this invention can be implemented even while blood is in a collection bag. Typically, procedures for disinfecting blood and blood products include washing blood or blood products in a disinfecting composition and then separating the blood or blood product from the disinfecting composition.

The concentration of oxidizing compound in the disinfectant composition and the time required to effectively inactivate any harmful substance present in the blood are dependent upon the disinfectant strength. Suitable concentrations and disinfecting times will become evident in the more detailed description of the invention and the exemplary embodiments.

Separating the oxidizing compound from the blood is accomplished by washing the disinfectant composition and blood in a suitable medium until the disinfectant is reduced to a safe or insignificant level. Preferably the medium is the same as that used to disinfect the red blood cells, plasma, or plasma product.

Further objects, features, and advantages of the present invention will become apparent to those skilled in the art from a consideration of the following detailed description.

DETAILED DESCRIPTION OF THE PREFERRED EMBODIMENT

The present invention involves the effective and safe disinfection of whole blood and blood products. The invention has wide application to all blood products such as whole blood for transfusion, blood cells, blood plasma and blood plasma proteins. Since whole blood is rarely used, the present invention is more particularly directed to processes for disinfecting red blood cells and blood plasma.

In accordance with the preferred method for disinfecting blood products, a method is provided in which viruses and bacteria including the HIV viruses, in whole blood and blood products are inactivated. Once disinfected the blood and blood products may be used for therapeutic or diagnostic purposes in a safe and effective manner. The invention is based upon the unexpected discovery that disinfectant compositions of oxidizing compounds which are substantially isotonic with blood do not lyse red blood cells or cause harm to blood products. Moreover, disinfectant compositions of oxidizing compounds which are not isotonic with respect to blood, and which until now have not been considered for use with blood products, can be used to disinfect plasma and plasma proteins without denaturing the protein or otherwise causing a substantial loss in physiological activity.

In accordance with the present invention, methods for disinfecting whole blood or blood products are provided which include the steps of providing a disinfectant composition of a disinfecting concentration of oxidizing compound and a diluent, and then mixing whole blood or blood product with the disinfecting composition for a length of time sufficient to inactivate any bacteria and virus present in the blood or blood product. After the blood or blood product is disinfected, the oxidizing compound is separated from the disinfecting composition, providing blood or blood product which is safe and effective for therapeutic or diagnostic use.

Suitable oxidizing compounds having utility in the practice of the present invention include but are not limited to chlorine dioxide, sodium tetraborate decahydrate, sodium perborate tetrahydrate, potassium permanganate, sodium nitrate, sodium persulfate, calcium hypochlorite, potassium chlorate, benzoyl peroxide, potassium nitrate, and sodium hypochlorite. When chlorine dioxide is the oxidizing compound utilized in disinfecting blood or blood products according to the present invention, the chlorine dioxide is preferably generated in situ by the reaction of sodium chlorite and a Brönsted acid or alternative chlorine dioxide generating reagents.

As described below, the above identified oxidizing compounds will effectively disinfect blood and blood products without substantial loss of physiological activity. It is also contemplated as being within the teachings of the present invention to disinfect blood or blood products with oxidizing compounds having sufficient oxidizing properties to inactivate viruses and bacteria. Thus, a wide variety of oxidizing compounds are available for disinfecting blood and blood products including chlorine, chloride of lime, inorganic oxo compounds, hypochlorous acid, chlorous acid and salts thereof, perchloric acid, potassium peroxodisulphate, sodium peroxide, barium peroxide, urea peroxohydrate, and alkali perborates.

Exemplary disinfectant compositions used for disinfecting whole blood or red blood cells according to the present invention include diluents in the form of aqueous solutions having an isotonic effective concentration of solute. For purposes of the present invention, isotonic effective concentrations are a concentration of suitable solute which renders the disinfectant composition substantially isotonic with blood. Those skilled in the art will appreciate that when the disinfectant composition includes sufficient oxidizing compound to contribute to the tonicity of the disinfectant composition, the isotonic effective concentration of any given solute is less than that required when the oxidizing compound does not significantly contribute to the tonicity of the disinfecting composition. Thus, when a disinfectant composition consists of less than 0.001 wt % sodium chlorite and less than 0.005 wt % Brönsted acid reacted to form chlorine dioxide, there is very little if any osmotic pressure contributed by oxidizing compound. In order to have an isotonic disinfectant composition in this case, the diluent itself is isotonic and includes solute sufficient to render the diluent isotonic.

On the other hand, when the disinfectant composition includes, for example, an aqueous solution of about 0.25 wt % sodium chlorite and about 0.2 wt % Brönsted acid which, react to form an oxidizing compound, the aqueous diluent requires less solute to render the disinfectant composition isotonic. In this case, the oxidizing compound provides some degree of tonicity to the aqueous disinfectant composition and the diluent can include less solute, for example 0.45 wt % sodium chloride. When disinfecting cellular blood products such as red blood cells, in accordance with the teachings of the present invention, the controlling factor is that the disinfectant composition have a tonicity which is sufficiently close to that of blood so that hemolysis is prevented.

In accordance with the present invention, suitable diluent solutes include any of a number of compounds used in the preparation of isotonic solutions. Exemplary solutes include but are not limited to sugars such as dextrose and glucose, polysaccharides such as dextran, albumin, and salts of alkali earth metals including sodium chloride, potassium chloride, and potassium bromide. Combinations of solutes known for their utility in storing physiological cells and tissue are also suitable and include such combinations as citrate-phosphate-dextrose, citrate-phosphate-dextrose-adenine, and saline-mannitol-dextrose-adenine. As described in greater detail below, the presence of at least one solute in the diluent in the form of a sugar is preferred because sugar contributes to the reduction of any methemoglobin, oxidized hemoglobulin, formed during the disinfecting process.

Advantageously, diluents having utility in the practice of the present invention for their isotonic characteristics can be combined. Combining diluents is particularly suitable when disinfecting red blood cells because commercial collective units of red blood cells are frequently stored in isotonic solutions containing anticoagulant, such as ACD (acid-citrate-dextrose), CPD (citrate-phosphate-dextrose), CPD-A (CPD- adenine). Thus, when disinfecting collective units of red blood cells stored in isotonic solutions of anti-coagulant, the disinfectant composition may be prepared in a different isotonic diluent, e.g., normal saline, and combined with the anti-coagulant solution.

Further in accordance the present invention, processes for disinfecting plasma or plasma products, such as plasma protein fractions, optionally utilize disinfecting compositions having no solute and in which the diluent is sterile water, water, distilled water or sterile and distilled water. Because plasma and plasma products do not contain tissue or other forms of cellular material, there is no compelling need to have an isotonic medium for maintaining cellular osmotic pressure.

Providing a disinfectant composition of oxidizing agent and diluent is accomplished by simply combining the selected oxidizing agent and diluent and gently stirring. In the case of the in situ formation of oxidizing agent, such as chlorine dioxide, the reagents are combined and then allowed to react for a short time to form the chlorine dioxide.

Mixing a disinfectant composition with blood or blood products can be performed by simply combining the blood or blood product and disinfectant composition in a suitable container with light agitation to assure sufficient interaction between the blood and disinfectant composition. Suitable containers include but are not limited to blood collection bags and blood storage apparatus. It is preferable, however, to utilize automated cell washing equipment known in the art and available from a variety of sources including Cobe.

In accordance with the present invention disinfecting effective concentrations of oxidizing compound and sufficient periods of time for disinfecting blood and blood products are primarily dependent upon the choice of oxidizing compound. It can also be appreciated that useful concentrations of oxidizing compound and periods of time for disinfecting are interdependent. Thus, oxidizing compound concentrations can be varied and a relatively small concentration of oxidizing agent can be a disinfecting effective concentration when mixed with blood or blood products for longer lengths of time. Conversely, when relatively larger concentrations of oxidizing agent are utilized in disinfectant compositions, the period of time sufficient to disinfect blood or blood products is less.

Suitable periods of time for disinfecting will become apparent when considering the detailed examples which follow this discussion. It is understood that disinfecting effective periods of time may be adjusted in accordance with known principles of chemistry to accommodate treatment of the whole blood or blood product while it is refrigerated or even heated. Generally, disinfecting times will range from as low as 30 seconds to as high as 30 minutes. The preferred times, however, are in the range of 5 minutes to 10 minutes. Care must be taken in using lower or higher temperatures to avoid damage to cells, blood or protein products from the exposure itself—or from the combination of conditions of temperature and disinfecting composition. Generally, room temperature conditions can be utilized, however, some products may require lower disinfecting temperatures.

Finally, the separating step includes thoroughly washing the disinfected blood or blood products with washing diluent for a length of time sufficient to remove substantially enough oxidizing compound to provide safe and physiologically active disinfected blood or blood products for therapeutic or diagnostic use. For separating red blood cells from the disinfectant, the disinfectant composition and red blood cell mixture is typically centrifuged while repeatedly adding volumes of washing diluent. Additionally, this separating step preferably further includes washing red blood cells in automated cell washing equipment such as that described above for mixing blood or blood products with a disinfectant composition. It should be noted that the use of cell washing equipment is not necessary when no or negligible residual disinfectant remains after centrifuging.

When separating disinfected red blood cells or disinfected whole blood in accordance with the present invention, washing diluent is preferably aqueous solutions which are substantially isotonic with blood. Such an aqueous solution can be the same diluent and solute utilized in the disinfectant composition. The term "substantially isotonic" is used to indicate that the disinfectant solution need not have an osmolality equal to that of blood but can be approximate to that of blood. Preferably, the washing diluent is a substantially isotonic aqueous solution which includes a sugar as a solute. As mentioned above and discussed in more detail below, the presence of at least one sugar in the washing diluent contributes to reducing any methemoglobin, formed during the disinfecting process to hemoglobin.

When separating disinfected plasma or disinfected plasma products such as plasma protein fractions in accordance with the present invention, washing diluent need not include solute and can be water, sterile water, distilled water or distilled and sterile water. However, it is within the scope of the present invention to utilize washing diluent which is substantially isotonic with blood for washing plasma and plasma products Additionally, when separating disinfected plasma protein fractions, the separating step preferably includes precipitating the plasma protein fractions as known in the art. For example, plasma proteins and plasma protein concentrates such as Factor VIII, Factor IX, antithrombin III, fibrinogen and immune globulins can be disinfected and then precipitated by contacting the disinfected plasma protein with an aqueous solution of about 80 wt % ammonium sulfate or similar precipitating agent.

Next, the disinfected and precipitated plasma proteins or plasma are resuspended in an aqueous solution which is preferably a solution which is isotonic with blood. Then, exhaustively dialyzing the resuspended plasma proteins or plasma against a relatively large volume of aqueous solution which is also preferably isotonic with blood reduces the concentration of oxidizing compound and precipitating agent. Alternatively, the dialyzing step may be replaced by high speed centrifugation using conventional techniques for separating proteins.

After the blood or blood product in the form of whole blood, red blood cells, plasma, and plasma protein fractions is disinfected and separated from the oxidizing compound, it is preferably stored the disinfected blood or blood product in an aqueous solution which incorporates a sugar. This is a particularly advantageous step when the disinfected blood product is red blood cells because the presence of sugar has been shown to contribute to the reduction of the small amount of methemoglobin to oxyhemoglobin, which can form from the oxidation of hemoglobin by the disinfecting composition.

Accordingly, by storing red blood cells, disinfected according to the teachings of the present invention, in storage solutions such, as adenine and saline (AS-3) or adenine-glucose-saline-mannitol (SAGM) the oxidized hemoglobin is converted back to oxyhemoglobin by enzymes indigenous to normal red blood cells, the NADH-diaphorase I and I, cytochrome $b_5$ and NADPH-linked methemoglobin-reducing system enzymes. As mentioned above, the practice of using sugar containing diluents in the disinfectant composition during the mixing and separating steps of the present invention additionally reduces the amount of methemoglobin formed during the disinfecting process. The presence of sugar at a concentration of as low as 0.1 wt % in the diluent and washing solution is effective. Thus, normal saline which incorporates 0.1 wt % dextrose is effective in reducing the amount of methemoglobin. Moreover, diluents and washing solutions which are rendered isotonic by the amount of sugar present such as 5 wt % dextrose can also be utilized.

It is contemplated as being within the scope of the present invention to repeat the mixing and separating steps. For example, after a unit of red blood cells is mixed with a disinfectant composition and separated from the oxidizing compound, the same unit can be repeatedly mixed with fresh isotonic disinfecting solutions. When minimal disinfecting times are used for each cycle, this technique increases the inactivation of any viruses or bacteria present.

Practicing this invention procedure is practical, useful, streamlined and economical. Its advantages particularly include eliminating transmission of viruses and micro-organisms in blood transfusions.

All of the foregoing operational principles and advantages of the present invention will be more fully appreciated upon consideration of the following detailed examples.

EXAMPLE 1

The following Example demonstrated that disinfecting solutions of chlorine dioxide formed in situ results in the formation of only small amounts of methemoglobin.

Thirty mL of fresh peripheral blood from a healthy donor was collected in a heparinized syringe. The blood was then centrifuged at 2,000 rpm to separate the red blood cells.

A disinfectant composition was prepared using the following procedure:

Three mL of a 15% aqueous lactic acid solution was added to 30 mL of aqueous normal saline. Then 3 mL of a 2.73% aqueous sodium chlorite solution was added to the lactic acid in normal saline solution. The disinfectant composition was allowed to sit at room temperature for 70 minutes and then it was diluted 1:10 in normal saline solution. The resulting disinfectant composition is 0.125% lactic acid and 0.023% sodium chlorite and generates chlorine dioxide.

A three mL aliquot of packed red blood cells which was separated from the whole blood during the centrifugation was mixed with 3 mL of the disinfectant composition. The red blood cell and disinfectant composition mixture was allowed to incubate at room temperature for 5 minutes.

A second three mL aliquot of packed red blood cells was mixed with another 3 mL of the disinfectant composition and allowed to incubate at room temperature for 10 minutes.

A third three mL aliquot of packed red blood cells was mixed with three mL of normal saline solution and utilized as a control.

Following the incubation step the red blood cells were separated from the two disinfecting solutions and the control solution by centrifuging and then washing four times with equal volume of normal saline solution.

All of the samples were then sent to a commercial laboratory for methemoglobin analyses which were determined as follows:

Control sample: 0.6% (within normal range of 3%)
Disinfected 5 min.: 6.6%
Disinfected 10 min: 6.2%

The above results probably are not physiologically significant. Moreover, the difference between the 5 minute and 10 minute exposure in negligible.

EXAMPLE 2

The following example illustrates the effect of storing red blood cells, disinfected according to the present invention, in sugar containing storage solution.

Twenty mL of fresh peripheral blood from healthy donors was introduced into a heparinized tube. The blood was centrifuged at 2,000 rpm to separate the red blood cells.

A disinfectant composition was prepared using the following procedure:

Three mL of a 15% aqueous lactic acid solution was added to 30 mL of aqueous 5% dextrose solution. Then 3 mL of a 2.73% aqueous sodium chlorite solution was added to the lactic acid in 5% dextrose solution. The disinfectant composition was allowed to sit at room temperature for 75 minutes and then it was diluted 1:10 in 5% dextrose solution.

Three mL of packed red blood cells which were separated from the whole blood during the centrifugation was mixed with 3 mL of the disinfectant composition. The red blood cell and disinfectant composition mixture was allowed to incubate for 3 minutes.

A control sample was treated by adding 3 mL of packed red blood cells to 3 mL of 5% aqueous dextrose solution and incubating for three minutes at room temperature.

Following the three minute incubation period for the disinfected sample and the control sample, the red blood cells were separated by centrifuging the samples. Then, each sample of separated red blood cells was washed four times with normal saline solution.

Following the washing step, the red blood cells in each sample were resuspended in citrate-phosphate-dextrose (1.7 g sodium citrate, 1.61 g dextrose, 189 mg citric acid, 140 mg monobasic sodium phosphate monohydrate) with added adenine. The ratio of citrate-phosphate-dextrose solution to adenine was 7.1:1. After incubating the red blood cells in this solution at room temperature for one hour, the samples were analyzed immediately for methemoglobin with the following results:

Control: 0.6% methemoglobin
Disinfected red blood cells: 0.9% methemoglobin

These results, when compared to the results obtained in Example 1, illustrate the effects of storing disinfected red blood cells in a suitable sugar containing storage solution. That is, any methemoglobin which is formed during the oxidizing process is apparently reduced

EXAMPLE 3

The following example illustrates the effect of the process of the present invention in inactivating bacteria present in red blood cells. This example also further illustrates the reduction in methemoglobin resulting from the use of sugar solutions.

Thirty mL of fresh peripheral blood from healthy donors was introduced into a heparinized tube. The blood was centrifuged at 2,000 rpm to separate the red blood cells.

A disinfectant composition was prepared using the following procedure:

Three mL of a 15% aqueous lactic acid solution was added to 30 mL of 0.45% saline solution. Then 3 mL of a 2.73% aqueous sodium chlorite solution was added to the lactic acid in 0.45% saline solution. This disinfectant composition was allowed to sit at room temperature for 90 minutes and then it was divided into three portions, each of which was diluted 1:10 with one of the following solutions:

Sample 1: 0.45% saline
Sample 2: 0.45% saline and 5% dextrose
Sample 3: 0.45% saline and 2% dextrose Three mL of packed red blood cells obtained as described above were inoculated with $E.\ coli$ (greater than $5 \times 10^5$). After the $E.\ coli$ and blood were mixed thoroughly a 50 microliter aliquot was plated on an appropriate plate. Then three mL of Sample 1 above was added to the inoculated red blood cells and allowed to incubate 3 minutes at room temperature.

Following the incubation, 50 microliters of the incubated red blood cells and disinfectant composition were plated on an appropriate plate. Then the disinfected red blood cells were separated by centrifuging and washed as described in Example 2. Another 50 microliter sample was plated on an appropriate plate.

The results of the above bacterial inoculum tests showed a small amount of red blood cell lysis, with minimal visible hemoglobin in the supernatant. After the plates were incubated overnight, the plate containing the inoculated sample not disinfected had grown bacterial colonies too numerous to count (greater the 10,000). The other two plates each showed from 100–200 colonies. These results indicate a dramatic reduction in $E.\ coli$ caused by the disinfectant composition.

In another phase of this experiment, two 3 mL samples of packed red blood cells were combined with three mL of Sample 2, and Sample 3 identified above. A third sample was maintained as a control and was mixed with 3 mL of normal saline. All of the samples were incubated for three minutes at room temperature and then separated by centrifuging and washed 4 times with the same diluent solution utilized in the final 1:10 dilution described above. All of the samples were immediately analyzed for methemoglobin. Following are the results:

Control: 0.8%
Sample 2: 1.8%
Sample 3: 4.2%

These results indicate that small amounts of methemoglobin is formed using oxidation type disinfectants with sugar solutions. Somewhat higher amounts of methemoglobin, but not clinically significant levels, form when lesser sugar is utilized.

EXAMPLE 4

The following example illustrates the effectiveness of disinfecting plasma according to the process of the present invention.

A disinfectant composition was prepared using the following procedure:

Three mL of a 15% aqueous lactic acid solution was added to 30 mL sterile water. Then 3 mL of a 2.73% aqueous sodium chlorite solution was added to the lactic acid in sterile water solution. This disinfectant composition was allowed to sit at room temperature and then it was diluted 1.10 with sterile water. A second sample of disinfecting solution was prepared in an identical manner except that the diluent was 5% aqueous dextrose solution.

Three mL of freshly heparinized human plasma was mixed with each of the above-described disinfecting compositions. After an incubation period, the protein were precipitated in 80% ammonium sulfate solution adjusted to pH 7.0. Then each of the samples were resuspended in either sterile water or in 5% dextrose solution in a volume equal to the initial volume. All sample, including a control which had not been disinfected, were immediately subjected to an electrophoresis study to determine any reduction in proteins in the plasma.

The protein electrophoretic patters were unchanged by the disinfecting process. The electrophoretic patterns of the various protein fractions were the same for the control as for the disinfected plasma indicating that the proteins had not been altered, as indicated in the Following Table I.

TABLE I

| Sample | Detected amount ng/dl. |
|---|---|
| 1. Control (exposure to 0.9 NaCl with no sterilant) | |
| Total protein | 8.1 |
| Serum protein albumin | 4.6 |
| Serum protein alpha | 0.2 |
| Serum protein alpha$_1$ | 0.8 |
| Serum protein beta | 1.4 |
| Serum protein globulin | 1.1 |

TABLE I-continued

| Sample | Detected amount ng/dl. |
|---|---|
| 2. Sterilant diluted in sterile water, incubated 5 minutes | |
| Total protein | 7.6 |
| Serum protein alpha | 0.2 |
| Serum protein alpha$_1$ | 0.8 |
| Serum protein beta | 1.2 |
| Serum protein globulin | 1.0 |
| Serum protein albumin | 4.4 |
| 3. Sterilant diluted in sterile water, incubated 10 minutes | |
| Total protein | 7.4 |
| Serum protein alpha | 0.2 |
| Serum protein alpha$_1$ | 0.7 |
| Serum protein beta | 1.2 |
| Serum protein globulin | 1.0 |
| Serum protein albumin | 4.3 |
| 4. Sterilant diluted in 5% dextrose (D5W), incubated 10 minutes | |
| Total protein | 7.5 |
| Serum protein alpha | 0.2 |
| Serum protein alpha$_1$ | 0.8 |
| Serum protein beta | 1.3 |
| Serum protein globulin | 1.0 |
| Serum protein albumin | 4.2 |

EXAMPLE 5

The following example illustrates the effect of disinfecting red blood cells with oxidizing compounds according to the present invention.

Sixty mL of fresh peripheral blood from healthy donors was introduced into a heparinized tube. The blood was centrifuged at 2,000 rpm to separate the red blood cells.

The following disinfectant compositions and a control solution were prepared by mixing the appropriate amount of oxidizing compound with normal saline diluent:
Sample 1: Normal Saline (0.9% NaCl as control)
Sample 2: 0.3 v/v % hydrogen peroxide
Sample 3: 0.1 v/v % Chlorox bleach (sodium hypochlorite)

Four mLs of packed red blood cells were added to each of the three samples identified above and incubated at room temperature of two minutes. Then each of the samples were centrifuged at 2,000 rpm to separate the red blood cells and wash with normal saline five times before a final centrifuging step.

A visual inspection of the supernatant for each of the samples indicates that no hemolysis has occurred. That is all the sample were clear and free of free hemoglobin. Additionally microscopic examination of cells taken from Samples 1-3 showed normal red blood cell morphology.

EXAMPLE 6

The following example illustrates the effect of disinfecting red blood cells with additional oxidizing compounds according to the present invention.

Sixty mL of fresh peripheral blood from healthy donors was introduced into a heparinized tube. The blood was centrifuged at 2,000 rpm to separate the red blood cells.

The following disinfectant compositions and a control solution were prepared by mixing the appropriate amount of oxidizing compound with normal saline diluent:
Sample 1: control
Sample 2: 0.10 wt % sodium tetraborate decahydrate ($Na_2B_4O_7 10H_2O$)
Sample 3: 0.10 wt % sodium perborate tetrahydrate ($NaBO_3 4H_2O$)
Sample 4: 0.10 wt % potassium permanganate ($KMnO_4$)

Each of the solutions was then diluted 1:100 in normal saline.

Four mLs of packed red blood cells were added to each of the three samples identified above and incubated at room temperature of three minutes. Then each of the samples were centrifuged at 2,000 rpm to separate the red blood cells and washed with normal saline four times and once with 0.45% saline and 3% dextrose solution before a final centrifuging step.

Portions of Sample 1 (control) and Sample 3 were analyzed for methemoglobin with the following results:
Sample 1: 0.6% methemoglobin
Sample 3: 1.1% methemoglobin A visual inspection of the supernatant for each of the disinfected samples indicated that no hemolysis occurred. That is all the sample were clear and free of free hemoglobin. Additionally microscopic examination of cells taken from Samples 1-3 showed normal red blood cell morphology.

EXAMPLE 7

The following example illustrates the effect of disinfecting red blood cells with additional oxidizing compounds according to the present invention.

Sixty mL of fresh peripheral blood from healthy donors was introduced into a heparinized tube. The blood was centrifuged at 2,000 rpm to separate the red blood cells.

The following disinfectant compositions and a control solution were prepared by mixing the appropriate amount of oxidizing compound with a diluent of 0.45 % saline and 5% dextrose:
Sample 1: control (diluent only)
Sample 2: 0.10 wt % sodium nitrate ($NaNO_3$)
Sample 3: 0.10 wt % sodium persulfate ($Na_2S_2O_8$)
Sample 4: 0.10 wt % calcium hypochlorite ($Ca(OCl)_2$)
Sample 5: Potassium chlorate ($KClO_3$)
Sample 6: Benzoyl peroxide ($(C_6H_5CO)_2O_2$)
Sample 7: Potassium nitrate ($KNO_3$)

Each of the solutions was then diluted 1:100 in 0.45% saline and 5% dextrose diluent.

Four mLs of packed red blood cells were added to each of the three samples identified above and incubated at room temperature of three minutes. Then each of the samples were centrifuged at 2,000 rpm to separate the red blood cells and washed with normal saline four times with 0.45% saline and 3% dextrose solution before a final centrifuging step.

Portions of Sample 1 (control) and Sample 4 were analyzed for methemoglobin with the following results:
Sample 1: 0.8% methemoglobin
Sample 3: 1.7% methemoglobin A visual inspection of the supernatant for each of the disinfected samples indicated that no hemolysis occurred with the exception of Sample 5 (potassium chlorate) which indicated a visible red discoloration without massive hemolysis. That is the sample were clear of free hemoglobin.

EXAMPLE 8

The following example illustrates the bacteriocidal activity of disinfecting compositions of oxidizing compounds.

An inoculum of *E. coli* (between $5\times10^5$ to $1\times10^6$) was added to four mL of packed red blood cells obtained in Example 7. After completely mixing the inoculum and the red blood cells, a 50 microliter aliquot was removed and plated on an LB plate.

Then 4 mL of the disinfecting composition identified as Sample 6 in Example 7 was diluted 1:100 with its diluent and added to the inoculated red blood cells. The mixture was allowed to incubate for three minutes at room temperature. Following the incubation a 50 microliter aliquot was removed and plated on an LB plate. Then the disinfected red blood cells were washed and centrifuged four times with a normal saline solution. Following the separation and washing steps a third sample of 50 microliters was removed and plated on a LB plate. All of the plates were incubated overnight at 37° C. and the colonies which had proliferated were counted.

After the overnight incubation the plate containing the sample taken from the inoculated red blood cells having no disinfectant treatment was confluent with bacterial colonies which were too numerous to count. The sample treated with the disinfectant composition but undergoing no washes had scattered colonies of less than 25. The disinfected sample which was washed and centrifuged four times also had only scattered colonies of about 40–50 per plate.

These results indicate that by initially washing red blood cells to remove accompanying adhered plasma protein, effective bactericidal effect of the disinfectant composition is evident. The fact that the same effect is obtained for a sample taken prior to centrifuging and washing indicates that bacterial kill is due to the added disinfectant composition and not due to centrifuging and removal of the added bacteria.

In addition to oxidizing compounds, it has been discovered that organic and inorganic Brönsted acids and bases are also have utility as disinfectants in the processes of the present invention. Accordingly, it is contemplated as being within the scope of the present invention to provide methods for disinfecting blood or blood products which include the steps of providing a disinfectant composition of a diluent and a disinfecting concentration of disinfectant selected from the group consisting of Brönsted acids and Brönsted bases. Then, mixing blood or blood products with the disinfecting composition for a length of time sufficient to inactivate any bacteria and virus present produces disinfected blood or blood product. Typically, after the blood or blood product is disinfected, the Brönsted acid or Brönsted base is separated from the disinfected blood or blood product, providing blood or blood product which is safe and effective for therapeutic or diagnostic use.

Suitable disinfectants are believed to be virtually any Brönsted acid and Brönsted base which form stable ambient condition aqueous solutions. These bases and acids include but are not limited to sodium phosphate, dibasic ($Na_2HPO_4$), sodium bicarbonate ($NaHCO_3$), carbonic acid ($H_2CO_3$), sodium dihydrogen phosphate ($NaH_2PO_4$), potassium hydroxide (KOH), hydrogen chloride (HCl), ammonium hydroxide ($N_4OH$), aspartic acid ($HO_2CCH_2C(NH_2)CO_2H$), and ascorbic acid.

Similar to the disinfecting compositions of oxidizing compounds described above, exemplary disinfectant compositions of Brönsted acid or Brönsted base used for disinfecting blood or red blood cells include diluents in the form of aqueous solutions having an isotonic effective concentration of solute. Solutes having utility in the diluents of the present invention are described above and are equally applicable for disinfecting compositions of Brönsted acids and bases.

Moreover, the methods for disinfecting blood and blood products utilizing disinfecting compositions of oxidizing compounds are equally applicable to methods for disinfecting blood and blood product utilizing compositions of diluent and Brönsted acid or Brönsted base. More particularly, when disinfecting plasma and plasma protein fractions, a suitable diluent is water, and the presence of solute in an isotonic effective concentration is not necessary. On the other hand, when disinfecting red blood cells, diluents should incorporate a solute which renders the disinfectant compositions isotonic with respect to blood.

The following non-limiting example illustrate the principles and advantages of utilizing disinfectant compositions of Brönsted acid or Brönsted base to disinfect red blood cells.

EXAMPLE 9

The following example illustrates the effect of disinfecting red blood cells with disinfectant compositions of Brönsted acid or Brönsted base according to the present invention.

Sixty mL of fresh peripheral blood from healthy donors was introduced into a heparinized tube. The blood was centrifuged at 2,000 rpm to separate the red blood cells.

The following disinfectant compositions and a control solution were prepared by mixing the appropriate amount of acid or base with a solution of 5% dextrose and 0.45% NaCl:

Sample 1: sodium phosphate, dibasic ($Na_2HPO_4$) at 0.10 wt %

Sample 2: sodium bicarbonate ($NaHCO_3$ at 0.10 wt %

Sample 3: carbonic acid ($H_2CO_3$)at 0.01 wt %

Sample 4; sodium dihydrogen phosphate ($NaH_2PO_4$) at 0.10 wt %

Sample 5: potassium hydroxide (KOH) at 0.01 wt %

Sample 6: hydrogen chloride (HCl) at 0.05M

Sample 7: ammonium hydroxide ($NH_4OH$) at 0.01 wt %

Sample 8: aspartic acid ($HO_2CCH_2C(NHI_2)CO_2H$) at 0.10 wt %

Sample 9: ascorbic acid at 0.01 wt %

In order to determine red blood cell viability and whether or not hemolysis occurs after exposure to the above described solutions of Brönsted acid and Brönsted base, a small aliquot of each of samples 1–9 was diluted 1:10. Then a 2 mL portion of packed red blood cells was mixed with an equal volume of each of diluted samples 1–9 and incubated at room temperature for 3 minutes. A 2 mL control sample of an aqueous solution of 0.45 wt % NaCl and 5 wt % dextrose was also prepared incubated with 2 mL of packed red blood cells.

After the 3 minute incubation period, the red blood cells and disinfectant solutions were centrifuged to separate the red blood cells. Then each of the separated red blood cells samples were washed four times with a 0.45 wt % NaCl and 5 wt % dextrose.

After each of the red blood cell samples was washed four times the disinfected red blood cells from each sample were examined for any signs of hemolysis. There was no visible signs of hemolysis when compared to the control sample. Furthermore, 45 minutes after the incubation period, the disinfected red blood cells remained intact and pelleted on re-centrifugation with supernatant discoloration.

EXAMPLE 10

The following experiment illustrates the utility of disinfectant compositions of diluent and Brönsted acids or Brönsted bases for inactivating bacteria.

A 2 mL portion of packed red blood cells was added to each of 19 vials. An inoculum of *E. coli* (between $9 \times 10^5$ and $1 \times 10^6$ bacteria) was added to 9 of the packed red blood cell samples and an approximately same inoculum of Streptococcus pneumoniae was added to another 9 of the packed red blood cell samples. A 30 microliter aliquot was taken from each vial and plated on appropriate media plates with one sample per plate.

Then one 2 mL portion of diluted Samples 1-9 of Example 9 was added to each of the inoculated packed red blood cells. This resulted in 9 pairs samples, with each pair having one inoculum of *E. coli* and one inoculum of Streptococcus and one disinfectant composition.

Each sample was gently mixed and incubated for four minutes at room temperature. Then a 30 microliter aliquot from each sample was plated on a media plate.

The remaining disinfected red blood cell samples were centrifuged and washed several times with normal saline to remove acid and base disinfectant. A third aliquot was removed from each sample and plated on a media plate. Finally, all plates were incubated overnight at 37° C. and colonies were counted the next morning.

The plates which were plated with inoculated red blood cells without disinfectant were completely covered with bacterial colonies, confluent, and too numerous to count.

The bacterial counts on the *E coli* inoculated plates were 50-125 colonies/plate for all disinfectant compositions with the exception of aspartic acid which failed to kill.

The bacterial counts on the *Streptococcus pneumoniae* inoculated plates were approximately 50 colonies/plate for all disinfectant compositions with the exception of aspartic acid (200 colonies/plate) and sodium phosphate (confluence, no kill).

The results indicate the effective gram-negative (*E. coli*) and gram-positive (*Streptococcus pneumoniae*) bactericidal reduction by exposure to acid and base compositions. The same bactericidical activity was observed prior to centrifugation of the samples so the observed effect cannot be due solely to physical removal of bacteria by centrifugation.

Having thus described preferred exemplary embodiments of the present invention, it should be noted by those skilled in the art that the disclosure herein are exemplary only and that alternative, adaptations and modifications may be made within the scope of the present invention. Accordingly, the present invention is not limited to the specific embodiments illustrated herein.

I claim:

1. A process for disinfecting red blood cells, said process comprising the steps of:
   providing a disinfectant composition consisting essentially of a disinfecting concentration of oxidizing compound and a diluent, said oxidizing compound being selected from the group consisting of sodium tetraborate decahydrate, sodium perborate tetrahydrate, potassium permanganate, sodium nitrate, sodium persulfate, calcium hypochlorite, potassium chlorate, benzoyl peroxide, hydrogen peroxide, potassium nitrate, and sodium hypochlorite and combination thereof said diluent being a solution of an isotonic effective concentration of solute, and said isotonic effective concentration being a suitable solute concentration which renders said disinfectant composition substantially isotonic with blood; and
   mixing red blood cells with said disinfecting composition for a length of time sufficient to inactivate any bacteria and virus present in said red blood cells; and
   separating said oxidizing compound from said blood cells, said blood cells being substantially viable for diagnostic or therapeutic use.

2. The method of claim 1 further including the step of separating said oxidizing compound from said red blood cells, said red blood cells being substantially viable for diagnostic or therapeutic uses.

3. The process of claim 2 wherein separating said red blood cells from said oxidizing compound is accomplished by washing said red blood cells with an isotonic aqueous washing solution of at least one sugar.

4. The method according to claim 1 wherein said oxidizing compound is selected from the group consisting of sodium tetraborate decahydrate, sodium perborate tetrahydrate, potassium permanganate, sodium nitrate, sodium persulfate, calcium hypochlorite, potassium chlorate, benzoyl peroxide, potassium nitrate, and sodium hypochlorite and combination thereof.

5. The process of claim 1 wherein said solute is selected from the group consisting of sodium chloride, sugars, polysaccharides, salts of alkali earth metals, and combinations thereof.

6. The process of claim 1 further including the step of storing said separated red blood cells in an isotonic aqueous solution of at least one sugar.

7. A process for disinfecting red blood cells said process comprising the steps of:
   providing a disinfectant composition consisting essentially of a diluent and a disinfecting concentration of Brönsted acid or Brönsted base selected from the group consisting of dibasic sodium phosphate, sodium bicarbonate, carbonic acid, sodium dihydrogen phosphate, potassium hydroxide, hydrogen chloride, ammonium hydroxide, and ascorbic acid, said diluent being an aqueous solution of an isotonic effective concentration of solute, and said isotonic effective concentration being a suitable solute concentration which renders said disinfectant composition substantially isotonic with blood;
   mixing red blood cells with said disinfecting composition for a length of time sufficient to inactivate any bacteria and virus present in said re blood cells; and
   separating said red blood cells from sufficient amounts of said disinfecting composition to provide whole blood red blood cells being substantially viable for diagnostic or therapeutic use.

8. The process of claim 7 wherein said solute is selected form the group consisting of sodium chloride, sugars, polysaccharides, salts of alkali earth metals, and combinations thereof.

* * * * *